(12) United States Patent
Nguyen

(10) Patent No.: US 7,101,966 B2
(45) Date of Patent: Sep. 5, 2006

(54) SELECTION OF PEPTIDE LIGANDS SPECIFIC FOR BACULOVIRUS DNA-BINDING PROTEIN FROM THE FLITRX™ RANDOM PEPTIDE DISPLAY LIBRARY

(75) Inventor: Khue Vu Nguyen, San Diego, CA (US)

(73) Assignee: Vista Biologicals Corporation, Carlsbad, CA (US)

( * ) Notice: Subject to any disclaimer, the term of this patent is extended or adjusted under 35 U.S.C. 154(b) by 96 days.

(21) Appl. No.: 10/945,402

(22) Filed: Sep. 21, 2004

(65) Prior Publication Data

US 2006/0063917 A1  Mar. 23, 2006

(51) Int. Cl.
*C07K 7/08* (2006.01)
*C07K 17/00* (2006.01)
*C12Q 1/70* (2006.01)
*G01N 33/68* (2006.01)

(52) U.S. Cl. .................. 530/327; 435/5; 435/DIG. 35; 436/86; 502/7; 530/810

(58) Field of Classification Search ...................... None
See application file for complete search history.

(56) References Cited

U.S. PATENT DOCUMENTS 6,037,135 A * 3/2000 Kubo et al. ................ 435/7.24

6,974,791 B1 * 12/2005 Wong et al. .................... 514/2

OTHER PUBLICATIONS

Laufs et al. Autographa californica Nuclear Polyhedrovirus Virus p143 Gene Product Is a DNA-Binding Protein. Virology. 1997, vol. 228, pp. 98-106.*

* cited by examiner

*Primary Examiner*—Jeffrey Edwin Russel

(57) ABSTRACT

Autographa californica nucleopolyhedrovirus (AcNPV) is a baculovirus widely employed as a vector for the expression of foreign genes and pest control. Although baculoviruses efficiently replicate in the nuclei of arthropod cells, the dynamics and mechanism of DNA replication within the infected cell are still poorly understood. Thus, to study such viral DNA replication, the availability of peptide ligands specific for DNA-binding protein (DBP) is needed. This work resulted in the selection of peptide ligands specifically binding to DBP for AcNPV from the FliTrx™ random peptide display library, which entails the amplification, cloning of the DBP gene from AcNPV, the construction of the expression plasinid for DBP, and the expression and purification of the recombinant His.Tag AcNPV DBP which was used as a target molecule for the selection of the peptide ligands. The affinity of peptide ligands was measured by ELISA procedures. The novelty and advantage of this invention is the monospecificity quality of the peptide ligands specific for AcNPV DBP which is valuable for diverse applications in basic as well as applied research.

2 Claims, 2 Drawing Sheets

SELECTION OF PEPTIDE LIGANDS SPECIFIC FOR BACULOVIRUS DNA-BINDING PROTEIN FROM THE FLITRX™ RANDOM PEPTIDE DISPLAY LIBRARY

FIELD OF THE INVENTION

*Bombyx mori* nucleopolyhedrovirus (BMNPV) and *Autographa californica* nucleopolyhedrovirus (AcNPV) belong to the Baculoviridae, a large family of viruses with double-stranded (ds) DNA genomes that are pathogenic mainly for lepidopteran insects. Both BmNPV and AcNPV are widely employed as vectors for the expression of foreign genes and pest control. The DNA-binding protein (DBP) is found to be an early gene product and appears to be crucial for viral DNA replication. The present invention is the procedure for the selection of peptide ligands that specifically bind to DBP from AcNPV (AcNPV DBP) using the FliTrx™ random peptide display library. The availability of such peptide ligands is valuable for diverse applications in basic as well as applied research.

BACKGROUND OF THE INVENTION

Baculovirus, including *Bombyx mori* nucleopolyhedrovirus (BmNPV) and *Autographa californica* nucleopolyhedrovirus (AcNPV), are a diverse family of arthropod viruses that are characterized by large (80 to 180 kb) circular double-stranded DNA (ds DNA) genomes and rodshaped enveloped virions. Both BmNPV and AcNPV are widely employed as vectors for the expression of foreign genes and pest control [1]. The advantage of the baculovirus-insect cell gene expression system in the protein production is that post-translational modifications are similar to those found in mammalian cells [2]. BmNPV has a 128,413 bp-long circular double-stranded DNA genome which encodes 136 potential genes [3]. The organization of the BmNPV genome closely ressembles that of AcNPV [4] which is the most extensively studied baculovirus. Mikhailov et al. [5] have purified and characterized a DNA-binding protein (designated DBP) from nuclear lysates of BmN cells (derived from *Bombyx mori*) infected with BmNPV. BmNPV DBP contains 317 amino acids and has an apparent molecular mass of 38 kDa. BmNPV DBP is encoded by the open reading frame 16 (ORF 16) located at nucleotides 16189 to 17139 in the BmNPV genome. This ORF is a homolog of AcNPV ORF 25 (96% homology), the product of which has not been identified so far. BmNPV DBP is found to bind preferentially to single-stranded DNA (ssDNA). The DNA binding site of DBP is estimated to be about 30 nucleotides per protein monomer. BmNPV DBP is capable of unwinding partial DNA duplexes in an in vitro system. Also, BmNPV DBP is found to be an early gene product during viral DNA replication (4–6 h postinfection) and it is one of the components of the multiprotein complex (with LEF-3 and IE-1) of the core replication machinery [6]. Thus, DBP appears to be crucial for viral DNA replication. Although baculoviruses, including BmNPV and AcNPV, efficiently replicate in the nuclei of arthropod cells, the dynamics and mechanism of viral DNA replication within the infected cell are currently poorly understood.

Mikhailov et al. [5] have purified the BmNPV DBP, and they, as well as Okano et al. [6] have studied the mechanism of viral DNA replication within the infected cell by using the rabbit polyclonal antibodies against an N-terminal six-His.Tag DBP. However, rabbit polyclonal antibodies are not adequate enough to recognize DBP specifically; monospecificity is needed to study the evolution of DBP and its role during viral DNA replication. Therefore, obtaining peptide ligands specific for DBP is necessary to address this issue, the reason for which the present research was initiated. Compared to the rabbit polyclonal antibodies against an N-terminal six-His.Tag DBP used by Mikhailov et al. [5] and Okano et al. [6], the peptide ligands specifically binding to DBP could be used as a valuable specific tool for diverse applications in basic as well as applied research.

The work reported herein provides the method for the amplification and cloning of the DBP gene from AcNPV, the construction of the expression plasmid for His.Tag AcNPV DBP, and its expression in BL21 (DE3) *E. coli* cells as well as the purification of the obtained recombinant His.Tag AcNPV DBP by using a column of Ni-NTA His.Bind$^R$ Resin. The obtained purified His.Tag AcNPV DBP is then used as a target molecule for the selection of the peptide ligands specific for DBP from the FliTrx™ random peptide display library.

The FliTrx™ random peptide display library technique has the most desirable properties of available peptide selection technologies [7]. Understanding interactions between macromolecules is a central theme of biology—with these molecules, complementary in the surface character and shape, usually defining both the specificity and the strength of mutual interactions. Previously, the best method for precisely defining these contact surfaces was to determine the tertiary structure of an interacting complex by X-ray diffraction or by multi-dimensional NMR techniques. However, these approaches are time consuming and are not always feasible. Smith [15] and other researchers [16, 17] thus tried to pioneer a different method and succeeded in enabling huge population of diverse macromolecules to be screened, and specific members of these populations were selected on the basis of their binding affinity to an immobilized target. In this technique, DNA sequences encoding highly diverse libraries of short peptides are fused to the 5'-ends of bacteriophage coat protein genes. Following expression, these fusions were folded and assembled, exposing the random peptides on the bacteriophage surface. The phage/peptide libraries were then given the opportunity to bind to an immobilized target protein, typically a monoclonal antibody; and phage displaying peptides that interact specifically with the target were selectively retained through a washing procedure. Retained phage particles were eluted and then submitted for additional technique; its variations were applied to map a wide range of protein-protein interactions [18–22]. Although the peptide sequence information derived from these studies is useful, the ability to perform structural studies on the obtained peptides is limited both by the low expression levels of phage coat protein genes and by the character of the peptides selected by these systems, which are usually unconstrained molecules possessing many degrees of conformational freedom. To address both of these problems, Lu et al. [7] recently developed an alternative to Smith's display method [15], the FliTrx™ random display library technique. This approach entails the use of the bacterial flagellum to display random peptide libraries on the surface of *E. coli*. The entire coding sequence of *E. coli* thioredoxin (trxA) was inserted into a dispensable region of the gene for flagellin (fliC), the major structural component of the *E. coli* flagellum. The resulting fusion protein (FliTrx) was efficiently exported and assembled into partially functional on the bacteria surface. A diverse library of random dodecapeptides was displayed in FliTrx on the exterior of *E. coli* as conformationally constrained insertion into the thioredoxin active-site loop, a location known to be a highly permissive site for the insertion of exogenous peptide sequences into native thioredoxin.

PURPOSE OF THE INVENTION

The purpose of the invention is to select peptide ligands that specifically bind to baculovirus DNA-binding protein (DBP) from AcNPV (ACNPV DBP) which entails the following procedure: 1/ Performing the amplification and cloning of the DBP gene from AcNPV; 2/ constructing the expression plasmid for AcNPV DBP using the pET-28a (+) transfer vector; 3/ performing the expression of His.Tag AcNPV DBP in BL21 (DE3) E. coli cells; 4/ performing the purification of the obtained recombinant His.Tag AcNPV DBP by using a column of Ni-NTA His.Bind$^R$ Resin; and 5/ performing the selection of the peptide ligands specific for AcNPV DBP from the FliTrx™ random peptide library by using the obtained purified His.Tag AcNPV DBP as a target molecule. The novel and advantageous aspect of this invention is obtaining peptide ligands specific for AcNPV DBP which thus offer the monospecificity quality that is lacking in the previously known use of the rabbit polyclonal antibodies against an N-terminal six-His.Tag DBP. The availability of the peptide ligands specific for AcNPV DBP is valuable for diverse applications—(a) in basic research, peptide ligands specifically binding to DBP could be used for the study of the dynamics of viral genome and its replication within the infected cell; and (b) in applied research, they could be immobilized on a chromatographic support for an improved affinity purification of AcNPV DBP, or they could be used for the development of a quantitative method for the determination of the presence of baculovirus in various samples as well as for the development of a peptide ligand based assay for the determination of baculovirus titers. Furthermore, due to the homology of sequences concerning DBP between BmNPV and AcNPV, the obtained peptide ligands specific for DBP could be used as a universal tool for the two viruses.

MATERIALS AND METHODS

Cell Line, Baculovirus and Culture Medium

Spodoptera frugiperda (Sf-9) cells (Pharmingen, San Diego, Calif.) were maintained as monolayer cultures in 25 cm$^2$ tissue culture flasks (353014; Falcon) at 28° C. in TNM-FH medium (Sigma-St. Louis, Mo.) supplemented with 0.35 g/l NaHCO$_3$, 10% fetal bovine serum (Sigma, St. Louis, Mo.), and 1% antibiotic-antimycotic (Gibco BRLR, Rockville, Md.). The Sf-9 cells were infected with AcNPV (Pharmingen, San Diego, Calif.) using the experimental conditions according to the manufacturer's recommendations. The isolation of AcNPV particles and AcNPV DNA was performed by using the procedures of the Baculovirus Expression Vector System (Instruction Manual, Pharmingen).

Amplification

The amplification of the AcNPV DBP gene was assessed by using the polymerase chain reaction (PCR) technique [8, 9]. Two synthesized oligonucleotides: Forward primer (SEQ ID NO. 1) and reverse primer (SEQ ID NO. 2) (Invitrogen, Carlsbad, Calif.), which generated appropriate sites (NdeI and BamHI sites) for the construction of the expression plasmid for AcNPV DBP, were used. They have the following sequences: 5' GGGGATCCGCAAGACATTTTGAC 3' (SEQ ID NO. 1) and 5' GGCATATGGCAACTAAACGCAA 3' (SEQ ID NO. 2)

The oligonucleotide SEQ ID NO. 1 was based on the sequence between base pairs 21135 to 21149 of the AcNPV-DNA described by Ayres et al. [10] (GenBank Accession No. NC_001623). The oligonucleotide SEQ ID NO. 2 was selected by taking the complementary sequence between base pairs 22117 and 22133 of the AcNPV-DNA described by Ayres et al. [10] (GenBank Accession No. NC_001623). Amplification was conducted by using a DNA Thermal Cycler (Amplitron$^R$ II Thermolyne). The reaction was conducted in a total volume of 50 µl with 2.5 U of Taq DNA polymerase (Promega Corporation, Madison, Wis.) in the presence of the PCR reaction buffer from Promega kit containing 0.1 nmol each of oligonucleotides, 10 pmol each of nucleotides dATP, dCTP, dGTP, and dTTP, 62.5 pmol of MgCl$_2$ (Promega Corporation, Madison, Wis.) and 30 ng of AcNPV DNA isolated previously. Amplification conditions were as follow: Denaturating at 94° C. for 1 minute, anneling at 55° C. for 2 minutes, and elongating at 72° C. for 1 minute, each for 35 cycles. The PCR product obtained was DBP-DNA which was analyzed by electrophoresis on a 20 g/l agarose gel to screen for the presence of the appropriate-size band using the fluorescent dye ethidium bromide. The PCR product DBP-DNA was then isolated and purified by phenol-chloroform extraction, dried and resuspended in distilled water according to the method described by Sambrook et al. [11].

Cloning

The obtained purified PCR product DBP-DNA was then subjected to the ligation reaction in the pCR$^R$ II plasmid vector of the TA Cloning kit (Invitrogen, Carlsbad, Calif.). The reagents of this kit and the reaction conditions used were according to the manufacturer's recommendations. The ligation product was then introduced in INVαF' E. coli strain by using the reagents and the transformation procedure of the TA Cloning kit (Invitrogen, Carlsbad, Calif.). The sequencing for inserts was performed by using blue-white color selection. The sequencing of the obtained inserts was performed by using the ABIDNA sequencer. The resulting vector was termed (1) (pCR$^R$ II/DBP-DNA).

Construction of the Expression Plasmid for AcNPV DBP

From the previously obtained vector (1), the EcoR I fragment containing the DNA coding sequences of AcNPV DBP was isolated and then digested with NdeI and BamHI. The resulting fragment containing the DNA coding sequences of DBP, DBP-DNA, was then isolated and subjected to the ligation reaction in the pET-28a (+) plasmid vector (Novagen, Madison, Wis.) predigested by NdeI and BamHI and predephosphorylated with calf intestinal alkaline phosphatase (Boehringer Mannheim, GmbH, Germany). The reaction was conducted in the presence of the reagents for the ligation of the TA Cloning kit (Invitrogen, Carlsbad, Calif.). The reaction conditions used were according to the manufacturer's recommendations. The ligation product was then introduced in INVαF' E. coli strain (Invitrogen, Carlsbad, Calif.) by using the reagents and the transformation procedure of the TA Cloning kit (Invitrogen, Carlsbad, Calif.). The screening for inserts was based on the presence of white colonies. The resulting vector thus obtained was termed (2) (pET-28a (+)/DBP-DNA).

Expression of Recombinant His.Tag AcNPV DBP, Purification and Western Blotting

The previously obtained vector (2) was transformed into BL21 (DE3) E. coli cells (Invitrogen, Carlsbad, Calif.). The reagents of this kit and the reaction conditions used were according to the manufacturer's recommendations. The screening for transformed BL21 (DE3) *E. coli* cells was based on the presence of white colonies. The obtained transformed BL21 (DE3) *E. coli* were then cultured in LB medium (Difco™ Luria Broth Base, Miller, from Becton, Dickinson and Company, Sparks, Md. 21152) supplemented with Kanamycin (25 μg/ml) (Sigma, St. Louis, Mo.). The transformed BL21 (DE3) *E. coli* cells were collected 2 hours after induction with 1 mM isopropyl β-D-thiogalactopyranoside (IPTG) (Sigma, St. Louis, Mo.) by centrifugation at 2,000×g for 20 minutes. The transformed cells were then resuspended in 50 mM Tris-HCL (pH 7.5) containing 150 mM NaCl, 1% triton$^R$ X-100, 10 mM imidazole, lysozyme (EC 3.2.1.17) from chicken egg white (3 mg/ml), and a set of protease inhibitors (1 mM phenylmethylsulfonyl fluoride, 0.71 mM AEBSF, 0.57 μM apronitin, 35 μM bestatin, 10 μM E-64, 14 μM leupeptin, and 7 μM pepstatin A) (Protease Inhibitor Cocktail Set III, Calbiochem-Novabiochem Corp., San Diego, Calif.), homogenized and lysed on ice for 30 minutes. The lysate was centrifuged at 30,000×g for 15 minutes. The resulting supernatant thus obtained (cleared lysate) was then loaded onto a 1 -ml column of Ni-NTA His.Bind$^R$ Resin (Novagen, Madison, Wis.) for the purification of His.Tag AcNPV DBP under native (non-denaturing) conditions. The reagents of this kit and the native conditions used were according to the manufacturer's recommendations. The SDS-NuPAGE$^R$ 4–12% Bis-Tris gel was performed as described by Laemmli [12]. The gel was fixed and stained with Coomassie brilliant blue and then electrophoretically transferred to Immuno-Blot™ PVDF membrane (Bio-Rad Laboratories, Hercules, Calif.) by using a semidry-blot apparatus (El 9001-XCell II™ Mini Cell, Novex) according to the manufacturer's guidelines. Western blots were probed with a 1:1,000 dilution of mouse monoclonal Ig $G_1$ antibody to penta-His™ (QIAGEN, Valencia, Calif.), washed, incubated with a ready-to-use solution of alkaline phosphate-conjugated, affinity purified, anti-mouse species IgG (Western Breeze™, Chemiluminescent Immunodetection System, Invitrogen), and developed by using the chemilumescent substrate (Western Breeze™, Chemiluminescent Immunodetection System, Invitrogen). The reagents of this kit and the Western blots conditions used were according to the manufacturer's instructions. After incubation for 5 minutes at room temperature, autoradiography was developed using the BIOMAX™ MR emulsion film (Eastman Kodak Co., Rochester, N.Y. 14650). The protein concentrations were determined by the Lowry method with bovine serum albumin as a standard [13].

FliTrx™ Random Peptide Display Library Selection

The obtained purified His.Tag AcNPV DBP was subjected to the immobilization on the polystyrene tissue culture dish (25025, 100×20 mm style) (Corning Glass Work, Corning, N.Y. 14831) (25 μg/ml) for the selection of the peptide ligands specifically against AcNPV DBP. The reagents and the selection conditions used were according to the manufacturer's instructions of the FliTrx™ random peptide display library kit (Invitrogen, Carlsbad, Calif.).

ELISA Protocols for His.Tag AcNPV DBP Screening

ELISA procedure was used for analysis of His.Tag AcNPV DBP as a target. The polystyrene microtitration plates (PolySorp™ Surface, Immuno™ Plate, Nunc) were used as the solid phase for the assay. All washes were performed four times with phosphate-buffered saline (PBS) containing 0.05% (V/V) Tween$^R$ 20 (PBS-T). The substrate solution for alkaline phosphatase (p-nitrophenyl phosphate, pNPP, 1 mg/ml, in 0.2 M Tris-HCl buffer, pH 7) was from Sigma, St. Louis, Mo. The reaction was stopped by the addition of 3 M NaOH (50 μl per well). The optical density at 405 nm (O.D.$_{\lambda=405\ nm}$) was measured in a microplate colorimeter (Molecular Devices, Thermo max Microplate Reader).

1. Using the FliTrx™ Protein Solution

Wells of the microtitration plates were coated with the FliTrx™ protein solutions obtained from induced culture cell of positive clones that contain the peptides recognized by His.Tag AcNPV DBP (50 μl per well). To account for plate binders, empty plates were used as negative controls. After incubation overnight at +4° C., the plates were washed, and the uncoated attachment sites on the plates were saturated by incubation for 1 hour at 37° C. with a solution of 2% nonfat dry milk in PBS-T: PBS-T-M (200 μl per well). The plates were then washed, and an aliquot of 100 μl (6 μg) of the purified His.Tag AcNPV DBP was added to both the target plate and the control plate. Plates were incubated for. 1 hour at 37° C. The plates were then washed, and 100 μl of a 1:1,000 dilution of mouse monoclonal Ig $G_1$ antibody to penta-His™ (QIAGEN, Valencia, Calif.) in PBS-T-M were added. After being incubated again for 1 hour at 37° C., the plates were washed, and 100 μl of a 1:1,000 dilution of goat anti-mouse IgG conjugated to alkaline phosphatase (Bio-Rad Laboratories, Hercules, Calif.) were added. After being incubated again for 1 hour at 37° C., the plates were washed, and substrate solution (200 μl per well) was added. After incubation for 1 hour at 37° C., the reaction was stopped.

2. Using the Biotinylated Synthesized Peptide Ligand

Wells of the microtitration plates were coated with 50 μl (2 μg) of purified His.Tag AcNPV DBP. To account for plate binders, empty plates were used as negative controls. After incubation overnight at +4° C., the plates were washed, and the uncoated attachment sites on the plates were saturated by incubation for 1 hour at 37° C. with PBS-T-M (200 μl per well). The plates were then washed, and an aliquot of 100 μl (25 μg) of the biotinylated synthesized peptide ligand No. 4 (SEQ ID NO. 6) (Invitrogen, Carlsbad, Calif.) was added to both the target plate and the control plate. Plates were incubated for 1 hour at 37° C. The plates were then washed, and 100 μl of a 1:1,000 dilution of mouse monoclonal IgG anti-biotin clone BN-34 conjugated to alkaline phosphatase (Sigma, St. Louis, Mo.) were added. After being incubated again for 1 hour at 37° C., the plates were washed, and substrate solution (200 μl per well) was added. After incubation for 30 minutes at 37° C., the reaction was stopped.

Results and Discussion

Amplification and Cloning of AcNPV DBP Gene

The results of the study show that the PCR product DBP-DNA of 1,012 bp of the AcNPV DBP gene was successfully amplified by two synthesized oligonucleotides SEQ ID NO. 1 and SEQ ID NO. 2 (FIG. 1). The obtained PCR product DBP-DNA was subcloned into the pCR$^R$ II plasmid vector of 3.9 kb (Invitrogen, Carlsbad, Calif.). The analysis of the sequence of inserts showed that the DNA sequence of the PCR product DBP-DNA completely matched with the sequences of AcNPV DBP gene described by Ayres et al. [10] (GenBank Accession No. NC_001623). The orientation of the Ac NPV DBP-DNA's insert in the plasmid vector (1) (pCR$^R$ II/DBP-DNA) was determined by the digestion of (1) with AccI and HindIII, the results of which show two fragments of 4,662 and 297 bp (data not shown).

Construction of the Expression Plasmid for AcNPV DBP

Prokaryotic host, especially *E. coli*, has been widely used for the expression of recombinant proteins. They offer several advantages as recombinant protein expression host including easy manipulation, rapid growth and simple media requirements. Prokaryotic expression systems are well suited for the expression of proteins that will be used in antibody production and for structural studies. In the prokaryotic expression systems, the T7 expression system is used. This T7 expression system allows high-level expression from the strong bacteriophage T7 promotor and T7 RNA polymerase; it is ideal for expressing soluble non-toxic recombinant protein in *E. coli* [14]. For this research work, the pET-28a (+) vector (Novagen, Madison, Wis.) is selected; this vector of 5.3 kb carries an N-terminal His.Tag/thrombin/T7Tag configuration plus an optional C-terminal His.Tag sequence. The histidine residues from the pET-28a (+) vector create a high-affinity metal binding site to allow purification of recombinant fusion proteins on nickel-chelating resin.

The presence of the DBP-DNA's insert in the plasmid vector (2) was confirmed by the digestion of (2) with NdeI and BamHI which gave two fragments of 5,328 and 1,012 bp (data not shown) and the DNA sequence of the released fragment of 1,012 bp completely matched with the sequence of AcNPV DBP gene described by Ayres et al. [10] (GenBank Accession No. NC_001623).

AcNPV DBP Expression and Purification

The expression of the His.Tag AcNPV DBP in BL21 (DE3) *E. coli* cells was visualized by Western blotting with mouse monoclonal IgG$_1$ antibodies raised against His.Tag DBP. The antibodies specifically recognized a protein with an apparent molecular mass of 40 kDa as well as in the cleared lysate (FIG. 2, lane 1) and in the eluate No. 6 (FIG. 2, lane 6). The absence of this polypeptide from the cleared lysate of non-transformed BL21 (DE3) *E. coli* cells suggested that it was of viral origin. This apparent molecular mass of 40 kDa for AcNPV DBP is similar to that found for BmNPV DBP (38 kDa) [5]. Therefore, the purified His.Tag DBP presumably encoded by the viral genome, obtained from the eluate No. 6 was used as a target molecule for the selection of the peptide ligands from the FliTrx™ random peptide display library.

FliTrx™ Random Peptide Display Library Selection

The results show that the FliTrx™ random display library technique [Lu et al., 7] was appropriately chosen for the purpose of the invention. The selection of peptide ligands specific for AcNPV DBP was successfully performed, and five dodecapeptides No. 1–5 (SEQ ID NO.: 3–7) recognized by the target molecule His.Tag AcNPV DBP were obtained. The sequences of these five dodecapeptides are as follow:

| No. 1: AGRKGERGSVLQ | (SEQ ID NO.3) |
| No. 2: AMLRAACVVRSM | (SEQ ID NO.4) |
| No. 3: ADYGKGLRRAMG | (SEQ ID NO.5) |
| No. 4: GGGGRRSGGACP | (SEQ ID NO.6) |
| No. 5: PAQAQTRRRRPR | (SEQ ID NO.7) |

Affinity between peptide ligands and target molecule His.Tag AcNPV DBP was measured by means of ELISA method. The obtained results show that the best affinity was found for the peptide ligand No. 5 with O.D.=1.35 (SEQ ID NO. 7) (see Table 1). The peptide ligands No. 1, 3 and 4 (SEQ ID NO. 3, 5 and 6) were found to have similar affinity, with O.D.=1.11–1.21 (see Table 1). The lowest affinity, O.D.=0.56, was found for the peptide ligand No. 2 (SEQ ID NO. 4) (see Table 1). These data indicate that the selected peptides exhibit a variety of binding strengths. The efficiency of such peptide ligands was found in the ELISA screening assay of His.Tag AcNPV DBP by using the biotinylated synthesized peptide ligand No. 4 (SEQ ID NO. 6), in which a mean O.D. value of about 4.0 was obtained with the target plate, compared to 0.30 obtained with the negative control plate.

CONCLUSION

The reported work described herein resulted in the successful selection of peptide ligands specific for AcNPV DBP, the affinity of which was measured by using ELISA procedures. The method used involved the amplification, cloning of the DBP gene from AcNPV, the construction of the expression plasmid for His.Tag AcNPV DBP, and its expression in BL21 (DE3) *E. coli* cells as well as the purification of the obtained recombinant His.Tag AcNPV DBP by using a column of Ni-NTA His.Bind$^R$ Resin. Five dodecapeptide ligands were recognized by the obtained purified His.Tag AcNPV DBP used as target molecule, by means of the FliTrx™ random display library technique.

In contrast to the old method of using the rabbit polyclonal antibodies against an N-terminal six-His.Tag DBP, the obtained peptide ligands specific for AcNPV DBP of the reported work offer the monospecificity quality which is currently needed in the field.

The availability of peptide ligands specific for AcNPV DBP made by the present invention is thus valuable for diverse applications. In basic research, these peptide ligands could be used for the study of the dynamics of viral genome and its replication within the infected cell. In applied research, they could be immobilized on a chromatographic support for an improved affinity purification of AcNPV DBP, or they could be used for the development of a quantitative method for the determination of the presence of baculovirus in various samples as well as for the development of a peptide ligand based assay for the determination of baculovirus titers. Moreover, because of homology of sequences concerning DBP between BmNPV and AcNPV, these peptide ligands could also be used as a universal tool for the two viruses.

REFERENCES

[1] S. Maeda, Expression of foreign genes in insects using baculovirus vectors, Ann. Rev. Entomol. 351 (1989) 351–372.

[2] C. D. Richardson, Baculovirus expression protocols, Methods Mol. Biol. 39 (1995) 25–63.

[3] S. Gomi, K. Majima, S. Maeda, Sequence analysis of the genome of *Bombyx mori* nucleopolyhedrovirus, J. Gen. Virol. 80 (1999) 1323–1337.

[4] S. Maeda, K. Majima, Molecular cloning and physical mapping of the genome of *Bombyx mori* nuclear polyhedrosis virus, J. Gen. Virol. 71 (1990) 1851–1855.

[5] V. S. Mikhailov, A. L. Mikhailov, M. Iwanaga, S. Gomi, S. Maeda, *Bombyx mori* nucleopolyhedrovirus encodes a DNA-binding protein capable of destabilizing duplex DNA, J. Virol. 72 (1998) 3107–3116.

[6] K. Okano, V. S. Mikhailov, S. Maeda, Colocalization of baculovirus IE-1 and two DNA-binding proteins, DBP and LEF-3, to viral replication factories, J. Virol. 73 (1999) 110–119.

[7] Z. Lu, K. S. Murray, V. V. Cleave, E. R. Lavallie, M. L. Stahl, J. M. McCoy, Expression of thioredoxin random peptide libraries on the *Escherichia coli* cell surface as functional fusion to flagellin: a system designed for exploring protein-protein interactions, Bio/Technology 13 (1995) 366–372.

[8] R. K. Saiki, S. Scharf, F. Faloona, K. B. Mullis, C. T. Horn, H. A. Erlich, N. Arnheim, Amplification of β-globine genomic sequences and restriction site analysis for diagnosis of sickle cell anemia, Science 230 (1985) 1350–1354.

[9] E. S. Kawasaki, A. M. Wang, Detection of gene expression. In PCR Technology; H. A. Erlich, Ed.; Stockton, New York, (1989) 89–97.

[10] M. D. Ayres, S. C. Howard, J. Kuzio, M. Lopez-Ferber, R. D. Possee, The complete DNA sequence of *Autographa californica* nuclear polyhedrosis virus, Virology 202 (1994) 586–605. (GenBank Accession No. NC_001623).

[11] J. Sambrook, E. F. Fritsch, T. Maniatis, Extraction, purification and analysis of messenger RNA from eukaryotic cells. In Molecular Cloning, a Laboratory Manual, $2^{nd}$ Ed.; Cold Spring Harbor Laboratory Press; Cold Spring harbor, N.Y., (1989) 7.28–7.52.

[12] U. K. Laemmli, Cleavage of structural proteins during the assembly of the head of bacteriophage T7, Nature 227 (1970) 680–685.

[13] O. H. Lowry, N. J. Rosebrough, A. L. Farr, R. J. Randall, Protein measurement with the folin phenol reagent, J. Biol. Chem. 193 (1951) 265–275.

[14] A. H. Rosenberg, N. L. Barbara, D. S. Chui, S. W. Lin, J. J. Dunn, F. W. Studier, Vectors for selective expression of cloned DNAs by T7 polymerase, Gene 56 (1987) 125–135.

[15] G. P. Smith, Filamentous fusion phage: novel expression vectors that display cloned antigens on the virion surface, Science 228 (1985) 1315–1317.

[16] S. F. Parmley, G. P. Smith, Antibody-selectable filamentous fd phage vectors: affinity purification of target genes, Gene 73 (1988) 305–318.

[17] J. K. Scott, L. Craig, Random peptide libraries, Curr. Opin. Biotechnol. 5 (1994) 40–48.

[18] J. Hammer, B. Takacs, F. Sinigaglia, Identification of a motif for HLA-DR1 binding peptides using M13 display libraries, J. Exp. Med. 176 (1992) 1007–1013.

[19] K. R. Oldenberg, D. Loganathan, I. J. Goldstein, P. G. Schultz, M. A. Gallop, Peptide ligands for a sugar-binding protein isolated from a random peptide library, Proc. Nat. Acad. Sci. USA 89 (1992) 5393–5397.

[20] J. K. Scott, D. Loganathan, R. B. Easley, X. Gong, I. J. Goldstein, A family of concanavalin A-binding peptides from a hexapeptide epitope library, Proc. Nat. Acad. Sci. USA 89 (1992) 5398–5402.

[21] S. Blond-Elguindi, S. E. Cwirla, W. J. Dower, R. J. Lipshutz, S. R. Sprang, J. F. Sambrook, M. J. H. Gething, Affinity panning a library of peptides displayed on bacteriophage reveals the binding specificity of BiP, Cell 75 (1993) 717–728.

[22] B. M. Djojonegoro, M. J. Benedik, R. C. Willson, Bacteriophage surface display of an immunoglobulin-binding domain of *Staphylococcus aureus* protein A, Bio/Technology 12 (1994) 169–172.

M: Marker (kb)

1: PCR product of the AcNPV DBP gene (1.012 bp)

Figure 1:
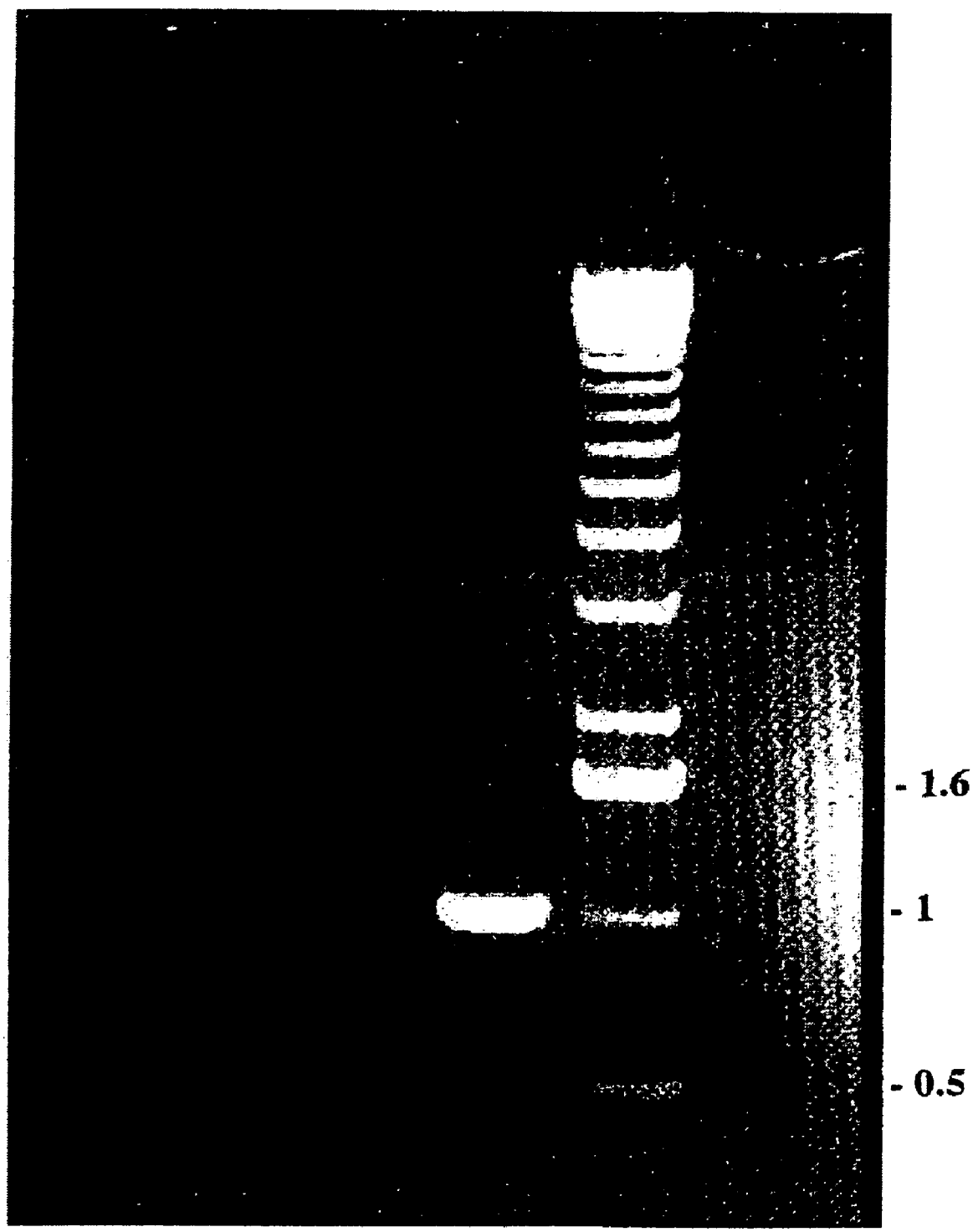
FIG. 1: PCR amplification of the AcNPV DBP gene.
Figure 2:
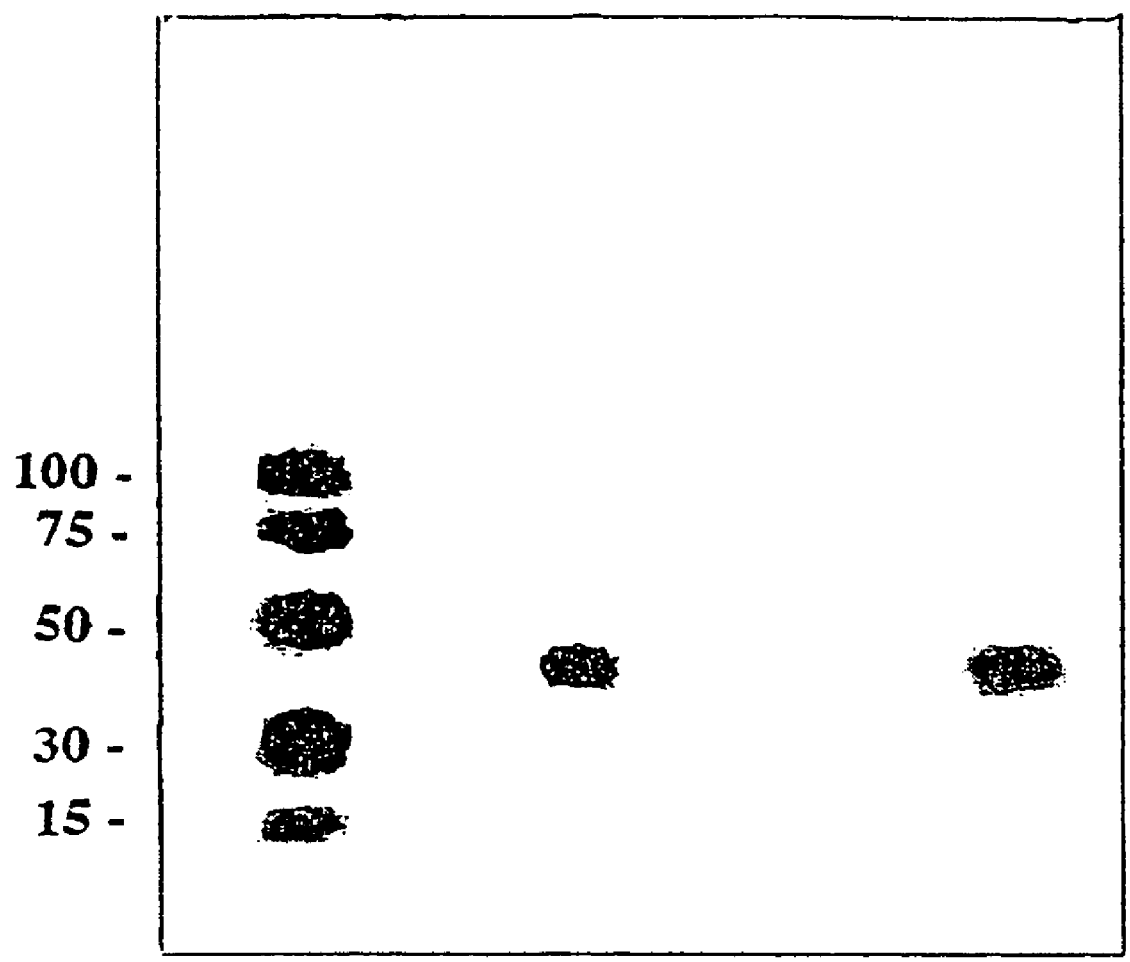

FIG. 2: Western blot analysis of the purification of His.Tag AcNPV DBP.

lane 1: Cleared lysate lane 2: Flowthrough lanes 3, 4: Washes lanes 5, 6, 7, 8: Fractions eluted M: Marker (kDa)

TABLE 1

Sequences of FliTrx ™ selected peptide ligands and variability in affinity for His.Tag AcNPV DBP determined by ELISA.

| Peptide ligands No. | Sequences of FliTrx ™ selected peptide ligands | SEQ ID NO. | ELISA[a] (O.D. $_{\lambda\ =\ 405\ nm}$) |
|---|---|---|---|
| 1 | A G R K G E R G S V L Q | 3 | 1.21 |
| 2 | A M L R A A C V V R S M | 4 | 0.56 |
| 3 | A D Y G K G L R R A M G | 5 | 1.11 |
| 4 | G G G G R R S G G A C P | 6 | 1.13 |
| 5 | P A Q A Q T R R R R P R | 7 | 1.35 |

[a]: The O.D. $_{\lambda-405\ nm}$ values are the mean of duplicate and the mean O.D. $_{\lambda-405\ nm}$ value of the negative controls is 0.14.

What is claimed is:

1. A peptide library comprising peptide ligands consisting of the sequences AGRKGERGSVLQ (SEQ ID NO:3), AMLRAACVVRSM (SEQ ID NO:4), ADYGKGLRRAMG (SEQ ID NO:5), GGGGRRSGGACP (SEQ ID NO:6), and PAQAQTRRRPR (SEQ ID NO:7).

2. A chromatographic support on which is immobilized the peptides AGRKGERGSVLQ (SEQ ID NO:3), AML-RAACVVRSM (SEQ ID NO:4), ADYGKGLRRAMG (SEQ ID NO:5), GGGGRRSGGACP (SEQ ID NO:6), and PAQAQTRRRPR (SEQ ID NO:7).

* * * * *

SEQUENCE LISTING

<160> NUMBER OF SEQ ID NOS: 7

<210> SEQ ID NO 1
<211> LENGTH: 23
<212> TYPE: DNA
<213> ORGANISM: baculovirus

<400> SEQUENCE: 1
ggggatccgc aagacatttt gac                    23

<210> SEQ ID NO 2
<211> LENGTH: 22

-continued

```
<212> TYPE: DNA
<213> ORGANISM: baculovirus

<400> SEQUENCE: 2
ggcatatggc aactaaacgc aa                                              22

<210> SEQ ID NO 3
<211> LENGTH: 12
<212> TYPE: PRT
<213> ORGANISM: baculovirus

<400> SEQUENCE: 3

Ala Gly Arg Lys Gly Glu Arg Gly Ser Val Leu Gln
1               5                   10

<210> SEQ ID NO 4
<211> LENGTH: 12
<212> TYPE: PRT
<213> ORGANISM: baculovirus

<400> SEQUENCE: 4

Ala Met Leu Arg Ala Ala Cys Val Val Arg Ser Met
1               5                   10

<210> SEQ ID NO 5
<211> LENGTH: 12
<212> TYPE: PRT
<213> ORGANISM: baculovirus

<400> SEQUENCE: 5

Ala Asp Tyr Gly Lys Gly Leu Arg Arg Ala Met Gly
1               5                   10

<210> SEQ ID NO 6
<211> LENGTH: 12
<212> TYPE: PRT
<213> ORGANISM: baculovirus

<400> SEQUENCE: 6

Gly Gly Gly Gly Arg Arg Ser Gly Gly Ala Cys Pro
1               5                   10

<210> SEQ ID NO 7
<211> LENGTH: 12
<212> TYPE: PRT
<213> ORGANISM: baculovirus

<400> SEQUENCE: 7

Pro Ala Gln Ala Gln Thr Arg Arg Arg Pro Arg
1               5                   10
```